United States Patent [19]

Pantano

[11] Patent Number: 5,550,127
[45] Date of Patent: Aug. 27, 1996

[54] METHOD OF TREATMENT FOR EIPH IN RACING STOCK

[76] Inventor: James A. Pantano, 2459 Riverbend Rd., Allentown, Pa. 18103

[21] Appl. No.: 524,834

[22] Filed: Sep. 7, 1995

Related U.S. Application Data

[*] Continuation-in-part of PCT/US94/04816, May 11, 1994.

[51] Int. Cl.⁶ .................... A61K 31/495; A61K 31/30
[52] U.S. Cl. .................. 514/248; 514/254; 514/393; 514/423; 514/929
[58] Field of Search ................. 514/423, 248, 514/254, 393, 929

[56] References Cited

U.S. PATENT DOCUMENTS

| | | | |
|---|---|---|---|
| 4,374,829 | 2/1983 | Harris et al. | 424/177 |
| 4,686,225 | 8/1987 | King | 514/283 |
| 4,722,334 | 2/1988 | Blackmen et al. | 128/203.16 |
| 4,955,372 | 9/1990 | Blackmen et al. | 128/203.16 |
| 5,128,355 | 7/1992 | Carini et al. | 514/381 |
| 5,132,118 | 7/1992 | Mills | 424/600 |
| 5,212,165 | 5/1993 | Aberg et al. | 514/114 |

FOREIGN PATENT DOCUMENTS 0012401  6/1980  European Pat. Off. .

OTHER PUBLICATIONS

Medline Abstract AW 89165550 (Nagai et al, Jul.–Aug. 1988).
Medline Abstract AW 94042697 (West et al, Sep. 1993).

*Primary Examiner*—Marianne M. Cintins
*Assistant Examiner*—Keith MacMillan
*Attorney, Agent, or Firm*—Shoemaker and Mattare, Ltd.

[57] ABSTRACT

The prevention and treatment of exercise-induced pulmonary hemorrhaging in non-human mammals is accomplished by the timely administration of effective amounts of vasodilators, including angiotensin converting enzyme inhibitors such as lisinopril, enalapril and captopril, and angiotensin II blocking vasodilators such as losartan potassium.

9 Claims, No Drawings

METHOD OF TREATMENT FOR EIPH IN RACING STOCK

This application is a U.S. continuation-in-part of International Application No. PCT/US94/04816, with an International Filing Date of May 11, 1994.

FIELD OF THE INVENTION

The present invention is directed to a method for preventing and treating exercise-induced pulmonary hemorrhage (EIPH) in non-human mammals by the administration of vasodilators to affected or potentially affected animals. Of particular interest is the use of vasodilators from the class of angiotensin converting enzyme (ACE) inhibitors in the prevention or treatment of EIPH in racing animals such as horses, camels, dogs and the like.

BACKGROUND OF THE INVENTION

Exercise-induced pulmonary hemorrhage (EIPH) is a condition common to a large percentage of racing and maximally exercised animals, particularly horses, and is defined by the appearance of blood in the lungs of the animal following a strenuous exercise routine.

A smaller percentage of these animals are commonly designated "bleeders" aptly describing the appearance of blood in the nostrils of the animal. This condition appears to be only symptomatic of the underlying source of the bleeding which originates as hemorrhaging in the lungs of the animal.

As current techniques have permitted, for example, with the use of fiber-optic endoscopes, veterinarians have determined that the source of the blood in the nostrils of the animal originates, for the most part, in the lungs of the animal and not from the nostrils as was previously thought.

Mills U.S. Pat. No. 5,132,118 elucidates much of the current theory, techniques and compositions used in the determination and treatment of EIPH.

The Mills patent describes the major lesions of EIPH as multiple, separate and coalescing foci of moderately proliferative small airway disease accompanied by intense neovascularization of the bronchial circulation. These lesions are bilaterally symmetrical and confined to the dorsal angle of the lungs. Lesion extension occurs only along the dorsum of the lungs. Microscopic examination of the lungs of horses dying of EIPH has revealed engorgement of the pulmonary arteries, veins and capillaries and rupture of the capillaries with hemorrhage into alveoli, bronchioles, bronchi, interstitium and subpleural tissue. The severity of engorgement and hemorrhage varied from almost nonexistent to massive in various areas of the lung, but the caudal portion of the lung lobes was the site of the most severe hemorrhage. Focally extensive pleural and interstitium fibrosis, and bronchiolitis were often accompanied by severe hemorrhage around large vessels and airways. Hemosiderophages also were present within this fibrous tissue, particularly at the junction of the pulmonary parenchyma and the deep layers of the pleura.

Numerous procedures have been performed in an attempt to prevent EIPH such as change in food, bedding or ventilation, application of external cold compresses to the nasal turbinate area, intermediate application of cold water over the thorax, and tying up the tail.

More recently, various parenteral agents have been utilized in an effort to diminish the magnitude of EIPH in racing or near maximally exercising horses, namely furosemide, atropine, estrogens, coagulants, clenbuterol, (VENTIPULMIN™), ipratroprium (ATROVENT™), cromolyn (INTAL™), intravenous saline infusion and steam inhalation. Hesperidin-citrus bioflavanoids administered orally do not alter the prevalence of the pulmonary hemorrhage. Enforced rest, with a convalescence length much longer than three months duration, does not change the repeatability of the EIPH episodes which recur upon resumption of training and upon attaining maximal exercise form.

The hereinbefore referenced U.S. Pat. No. 5,132,118 is directed to the prevention or treatment of EIPH in a equine specimen by administering a mixture of urea, alkaline potassium salts and optionally magnesium salts. Neither the use of ACE inhibitors nor the theory required to contemplate the use of such compounds in the prevention or treatment of EIPH is recognized in this patent.

Other patents which disclose various treatments for EIPH include Blackmer et al. U.S. Pat. Nos. 4,722,334 and 4,955,372. These patents are directed to the administration, via inhalation, of a humidified gas stream as a treatment for horses including a treatment for EIPH. These patents also do not contemplate ACE inhibitors in treatments for EIPH.

Angiotensin Converting Enzyme (ACE) Inhibitors

Lisinopril

Enalapril—carboxyalkyl dipeptide derivative

Zofenopril

Fosinopril—proline derivative

Captopril

Teprotide

Reatiapril or Fentipril or Pivopril

Ceranapril

Cetapril

Ramipril

Cilazapril

Indalapril

Indolapril

Spirapril

Perindopril

Quinapril

Other Vasodilators

Hydralazine

Prazosin

Losartan

The currently held theories regarding the etiology of EIPH do not fully contemplate the fundamental causative influences for this condition. The most common treatments for EIPH in the Thoroughbred horse racing community is the use of sulfamoyl-anthranilic acid derivatives, for example, furosemide (LASIX™) and ethacrynic acid which are parenterally administered to horses prior to racing. The use of these drugs treats EIPH as a cardiac disorder while other post-race treatments such as antibiotics, bronchial lavage and/or the avoidance of inhaled antigens are more directed to treating EIPH as a pulmonary disorder. Specifically directed therapy for addressing the causative conditions which precipitate the onset of EIPH have not, to date, been put forward.

Currently, the sulfamoyl-anthranilic acid derivatives, for example, furosemide (LASIX™) and ethacrynic acid, are parenterally administered to horses prior to racing in an attempt to control EIPH. Both of these drugs are potent diuretics which cause marked circulatory volume contraction in horses. The efficacy of these drugs in preventing EIPH has been extensively evaluated with widely variable results—sometimes stopping the hemorrhage, other times not stopping the hemorrhage, and yet other times reducing the severity of the hemorrhage but not stopping the hemorrhage. Administration of these diuretics to horses having EIPH did not influence either the racing time or the systemic circulation physiology, if given more than an hour prior to race time. However, administration of furosemide to horses negative for EIPH may have enhanced racing performance.

OBJECTS OF THE INVENTION

It is therefore an objective of the present invention to identify and treat the underlying cause of EIPH in non-human mammals.

SUMMARY OF THE INVENTION

A method for the treatment or prevention of pulmonary hemorrhage in a non-human mammal comprising administering to the non-human mammal an effective amount of at least one compound selected from the class of compounds of vasodilators, more particularly, the treatment or prevention of EIPH is preferred by the administration of an effective amount of at least one angiotensin converting enzyme inhibitor selected from the group consisting of lisinopril, enalapril and captopril to a non-human mammal such as horses, camels and dogs. Other vasodilators include hydralazine, prazosin and losartan.

DETAILED DESCRIPTION OF THE PREFERRED EMBODIMENTS

EIPH is believed to be the result of transient elevation of pulmonary capillary wedge pressure (PCWP) to levels compatible with pulmonary edema. The mechanism of such an elevation is due to transient left ventricular (LV) dysfunction secondary to inappropriate elevation of peripheral vascular resistance which is induced by sudden maximal exercise.

In humans, as well as in horses, there is typically a sudden increase in peripheral vascular resistance, afterload, resulting in the elevation of both systolic and diastolic BP, that occurs within seconds of the beginning of exercise. The subject's individual vasomotor response to exercise, propensity to high blood pressure, state of physical conditioning, level of anxiety, severity and type of heart disease as well as many other factors governs what happens subsequently. Even young subjects in good physical condition display a temporal dispersion as to when exercise-induced peripheral vasodilatation results in a levelling off of progressive increases in systolic pressure and a fall of dialostic pressure back to or below baseline. Some subjects exhibit this immediately, some after a minute or two and others only after 5 or more minutes of relatively low work loads. Starting the exercise at high, or maximal, work loads exaggerates both the temporal dispersion and the degree of blood pressure, or afterload, variation. There is a current body of opinion that the "second wind" while running and occurs when exercise induced peripheral vasodilation occurs, resulting in a sudden drop in left ventricular end-diastolic pressure (LVEDP), and PCWP and an increase in cardiac output. This almost always occurs after several minutes of full exertion.

A horse race is an immediate maximal effort lasting less than 2 minutes. Some horses may not vasodilate in time and develop a sudden increase in pulmonary wedge pressure, causing a low grade pulmonary edema and subsequent hemorrhage. Variations in upper airway construction and negative tracheal air way pressures may also add to the alveolar stress.

Ultimately, a combination of events may be responsible for causing EIPH in animals. It appears that these events may act synergistically to cause recurrent EIPH. The following factors are of primary importance.

1. Inappropriate lack of exercise induced peripheral vasodilation or even inappropriate exercise induced peripheral vasoconstriction causing high pulmonary artery pressure (PAP), PCWP, pulmonary capillary pressure (PCP) forcing fluid and blood into alveolar spaces and small bronchioles.

2. Large negative airway pressures are transmitted all the way down to the small airways and alveoli facilitating inward movement of fluid and blood. This will be aggravated by abnormalities in upper air way construction. Perhaps some anatomies, such as a dropped palate are sufficient by themselves to cause bleeding without the animal generating abnormally high LVEDP's or PCWP's—and this condition cannot be alleviated by afterload reducers.

3. Inflamed endothelium or bronchial mucosa, and perhaps areas of tissue granulation from the irritation of previous bleeds, forming the "soil" for a mucosa that will bleed at lower PCWP's.

Horses with a predilection to "bleed" during a race and pretreated with an afterload reducer, such as with ACE inhibitors, including lisinopril, enalapril or captopril, are more likely not to suffer the sudden induction of inappropriate peripheral vasoconstriction.

Because volume depletion and shrinking end-diastolic volume (EDV) reduces cardiac performance, the current therapy (LASIX™) is actually counterproductive since it does not address the basic etiology of the exercise induced breathing disorder. Potent diuretics, such as LASIX™, cause marked circulatory volume contraction in horses, and therefore negatively impacts peripheral perfusion and likely impedes the normal transfer of electrolytes across cell membranes that are critical to enzymatic and contraction events within the muscle cell.

Additionally, the efficacy of these diuretics in preventing EIPH has been extensively evaluated with widely variable results—sometimes stopping the hemorrhage, other times not stopping the hemorrhage, and yet other times reducing the severity of the hemorrhage but not stopping the hemorrhage.

The basic etiology of EIPH is believed by the Inventor to be transient LV dysfunction due to an acute and inappropriate elevation of peripheral vascular resistance, i.e., after load. Consequently, the treatment should be directed toward peripheral vasodilation and not to volume contraction.

The elevation of the PCWP as previously mentioned, has been found to be blunted by pretreatment with a vasodilator such as an ACE inhibitor and in particularly lisinopril, enalapril or captopril or combinations thereof.

One class of vasodilators which find application for EIPH may be any of the effective compounds selected from the group consisting of angiotensin converting enzyme (ACE) inhibitors including those described in U.S. Pat. No. 4,374,829 and EP 12,401 which are incorporated herein by reference in their entirety.

The preferred embodiment of the present invention for treatment of EIPH is the use of any effective angiotensin converting enzyme inhibitor, including compounds selected from the group consisting of:

Lisinopril

Enalapril—carboxyalkyl dipeptide derivative

Zofenopril

Fosinopril—proline derivative

Captopril

Teprotide

Reatiapril or Fentipril or Pivopril

Ceranapril

Cetapril

Ramipril

Cilazapril

Indalapril

Indolapril

Spirapril

Perindopril

Quinapril

Other preferred vasodilators which are not in the ACE inhibitor group include hydralazine, prazosin, and losartan. Prazosin blocks smooth muscle postsynaptic alpha$_1$ receptors. Losartan and its principle active metabolite block the vasoconstrictor and aldosterone-secreting effects of angiotensin II by selectively blocking the binding of angiotensin II to the AT$_1$ receptor found in many tissues. Angiotensin II is a potent vasoconstrictor and it is formed from angiotensin I in a reaction catalyzed by angiotensin converting enzyme (ACE, kininase II). Losartan potassium is a non-peptide molecule having the chemical name 2-butyl- 4-chloro-1-[p-(o-1H-tetrazol-5-ylphenyl)benzyl]imidazole-5-methanol monopotassium salt and it is available from Merck & Co., Inc. as Cozaar®.

In a preferred embodiment, the ACE inhibitors used in the prevention or treatment of EIPH in non-human mammals are selected from the group of lisinopril, enalapril and captopril.

The referenced U.S. patents are directed to lisinopril, enalapril and their derivatives, which are useful compositions in the application of this invention, and are herein incorporated by reference in their entirety.

The subjects used both in testing and treating with ACE inhibitors do not have to be actively racing, but only capable of putting forth an effort similar in degree of exertion and duration, such as in racing type conditions.

In testing, there are equal recruits from the "bleeder" and "nonbleeder" category. Subjects are cared for, fed and bedded by standard protocol for at least 2 weeks prior to testing.

A pulmonary artery flow directed catheter (Swan Ganz Catheter) is introduced by sterile technique by standard jugular approach and manipulated to the wedge (PCW) position, as will be more fully described hereinafter. After documentation of resting wedge and pulmonary artery pressures, the balloon is deflated and the end-hole attached to a pressure-sensing gauge capable of measuring PAP and PCW pressures when the balloon is inflated and propelled into the wedge position by the catheterizer. Cardiac output (CO) can also be measured.

The administration of LASIX™ may be used in combination with ACE inhibitors, in some cases, for evaluating synergistic, deleterious or other effects the combinations may have on an individual.

The horse participates in all out effort similar to true racing conditions. PCWP is measured every 15 seconds for the duration of the run, the pressure measurement is stored for later review.

The responses of PCWP to exercise is tabulated to determine if the mean change in PCWP during exercise among bleeders is greater than among nonbleeders.

After an appropriate period of recovery, bleeders with exercise induced elevation of PCWP are pretreated with ACE inhibitors such as lisinopril, enalapril or captopril and then are retested 7 days after institution of drug therapy.

Proposed Dosing Schedule

Lisinopril—20 mg qAM×3 days and then 40 mg qAM×4 days or

Enalapril—10 mg twice a day for 3 days and then 20 mg twice a day for 4 days

Captopril—may be considered in a dose of 50 mg 2 hours before race time

Of course, there are many variations which may be employed in the administration, monitoring and dosing regiments of ACE inhibitors in treating EIPH. These include the use of hemodynamic monitoring of bleeders with and without pretreatment with LASIX™, combined LASIX™ and vasodilator therapy in bleeders, alternate vasodilators (hydralazine, prazosin and losartan) and chronic versus prerace single dose therapies.

A Swan-Ganz (SG) catheter is passed through a vein into the heart and out into the pulmonary artery (PA). The balloon is inflated and subsequently floats to the limits of the chambers and vessels still big enough to accommodate the size of the catheter tip and inflated balloon. The catheter design and final position in the PA allows the operator to measure the most coveted pressure in all of cardiac hemodynamics—the left ventricular end-diastolic pressure (LVEDP). This is the pressure the left ventricle (LV) muscle feels in the instant prior to contraction and is the major defining factor that determines how hard the heart will squeeze for that heart beat. It is this characteristic of myocardial muscle that allows the heart to pump out all the blood that can flow into it without failing.

The SG catheter can measure this pressure because:

1) For blood to flow into the LV during diastole, the left atrial pressure (LAP) must be at least 1 mm more than LV diastolic pressure at all times during diastole. At the beginning of diastole, as the mitral valve opens, the LV has just squeezed out all the blood it wants to and, in the human, has lowered the early diastolic pressure to about 5 mm of Hg. Blood flows into a slightly noncompliant LV—it has mass so it can not have infinite compliance. As diastole proceeds, the in flowing blood causes a slight pressure increase to about 12–15 mm at end diastole. Normal healthy humans have an LVEDP of about 5–8 mm standing and about 10–12 mm lying flat. At these normal pressures, the LV will exert an average squeeze—enough to eject roughly 60% of its volume into the aorta at a pressure of 120 mm. As an aside, the aortic pressure falls during diastole as blood flows out to the periphery to about 80 mm. If blood flow increases and more blood flows into the LV, the LVEDP will rise slightly as the elasticity of the LV is stretched further by the extra blood. A tiny increase in LVEDP will instantly increase LV contractility out of proportion to the increase of LVEDP and all the extra blood will be handily pumped out. A normal human LV has maximal performance at LVEDP of about 15 mm. It is almost impossible to get this pressure higher than 20 mm in a normal heart no matter how much fluid one adds to the system. The normal healthy heart will pump it out. If the pressure ever gets up to or past 25 mm, the lungs will flood with frothy blood tinged fluid, i.e., pulmonary edema. This is the hallmark of congestive heart failure (CHF)—a diseased heart cannot keep the LVEDP down below 18 when stressed with a little extra fluid.

One way to stress a normal heart so that it transiently acts like a failing heart is to raise outflow resistance so high that physiologic contractile limits are exceeded and the LV can not pump against the outflow resistance. The result is that if a normal human heart is subject to severe high blood pressure—especially sudden severe hypertension—it could suddenly fail, meaning that the LVEDP goes above the 18–20 mm range and threatens to cause pulmonary edema. Human pulmonary capillaries fail at a pulmonary capillary pressure (PCP) of about 25–30 mm.

The LVEDP is measured from the right side by introducing a catheter in the right heart and wedging the end hole of a catheter in a pulmonary artery branch.

2) It has been well proven that if a catheter tip is jammed (wedged) into a branch of the pulmonary artery so that no blood can pass it—thereby shielding the vessel beyond the impacted catheter, all the vessels beyond the wedged catheter tip act like an extension of a fluid filled catheter.

Knowing the LA pressure allows one to infer that the LVEDP can be only a fraction of a mm less (assuming no other obstruction in the circuit such as problems with the construction of the smaller pulmonary vessels or blockage at the LV inflow valve, (mitral valve)).

Finally, the resistance to outflow of the LV is measured by a simple formula. The systemic vascular resistance (SVR) is the critical measurement of our experiment. It may be too high in a racing horse, causing the LV to temporarily fail and cause Exercise Induced Pulmonary Hemorrhage.

The formula is: SVR=(MAP–CVP)/CO where the SVR means systemic vascular resistance, MAP means the mean arterial blood pressure, CVP means the average central venous pressure and CO means cardiac output.

The arterial blood pressure is measured directly with another catheter inserted in any convenient artery. The CVP is measured from another port on the SG. The CO is also measured from the SG by the measurement of temperature differences during injection of a cold water bolus.

The following examples will illustrate the practice of the invention and demonstrate the effective use of ACE inhibitors on race horses known to be suffering from EIPH.

EXAMPLE 1

The drug lisinopril was administered to a known bleeder where all other parameters regarding the pre-exercise and post-exercise routines remained unchanged.

The horse was a 3-year-old filly, who had bled on her last workout before her first race. LASIX™ had been administered prior to this first race. She bled during the first race as well as the next 2 races which she ran. On LASIX™, she only bled in the "mild" range based on bronchoscopy.

Lisinopril was administered in 20 mg/day doses for 2 weeks. She then ran her 4th race and did not bleed as confirmed by bronchoscopy.

The practice of the invention is further illustrated by the following example.

EXAMPLE 2

A 5-year-old gelding was known to be such a bad bleeder that his racing career was severely impaired. He first bled during his second race at the age of 3, confirmed by bronchoscopy. He thereafter raced on LASIX™ but repeatedly bled in the mild to moderate range during most of his races, usually confirmed by bronchoscopy. He was subjected to repeated courses of antibiotics, removal of straw from his stall and hay from his diet. He was given a highly processed feed to minimize dust and chaff. He had repeated bronchial lavage with steroids and non-steroidal anti-inflammatory drugs. He still bled so frequently that he was sold off to a less competitive race track.

At that track, he continued to bleed during races despite LASIX™. The horse then started to bleed during his simple morning training gallops. He was given a 6 month lay off and came back as a 5-year-old and bled during his first race back, despite LASIX™.

The horse was then started on lisinopril 20 mg/day for 3 weeks and during those 3 weeks no longer bled during morning exercise sessions or during timed work outs. The trainer commented that she has never known the horse to go that long without bleeding. He has not yet run a race on lisinopril.

The invention has been described with respect to specific compositions and methods together with the functionalities described. The scope of the invention is therefore to be limited only to the scope of the appended claims and compositions, compounds and methods having the equivalent functionality and result, interpreted in view of the prior art that is pertinent to the claimed invention.

What is claimed is:

1. A method for the treatment or prevention of exercise-induced pulmonary hemorrhage in a non-human mammal comprising:

administering to said non-human mammal an effective amount of at least one angiotensin converting enzyme inhibitor.

2. A method for the treatment or prevention of exercise-induced pulmonary hemorrhage in a non-human mammal comprising:

administering to said non-human mammal an effective amount of at least one angiotensin converting enzyme inhibitor selected from the group consisting of lisinopril, enalapril and captopril.

3. The method of claim 2, wherein the non-human mammal is selected from the group consisting horses, camels and dogs.

4. A method for the treatment or prevention of exercise-induced pulmonary hemorrhage in a equine specimen comprising:

administering to said equine specimen an effective amount of at least one angiotensin converting enzyme inhibitor.

5. The method of claim 4, wherein said angiotensin converting enzyme inhibitor is selected from the group consisting of lisinopril, enalapril and captopril.

6. A method for the treatment or prevention of exercise-induced pulmonary hemorrhage in a non-human mammal comprising:

administrating to said non-human mammal an effective amount of at least one vasodilator selected from the group consisting of hydralazine, prazosin, losartan and mixtures thereof.

7. A method according to claim 6, wherein the vasodilator is losartan.

8. A method for the treatment or prevention of exercise-induced pulmonary hemorrhage in a non-human mammal according to claim 6, wherein the non-human mammal is selected from the group consisting of horses, camels and dogs.

9. A method for the treatment or prevention of exercise-induced pulmonary hemorrhage in a non-human mammal according to claim 8, wherein the non-human mammal is a horse.

* * * * *